United States Patent [19]
Lansink-Rotgerink et al.

[11] Patent Number: 5,824,825
[45] Date of Patent: Oct. 20, 1998

[54] PHOSPHORIC ACID CATALYST AND ITS USE

[75] Inventors: Hermanus Lansink-Rotgerink, Glattbach; Harald Hoecker, Sulzbach; Stefan Wieland, Offenbach; Steffen Seebald, Grosskrotzenburg; Heike Riedemann, Moembris, all of Germany

[73] Assignee: Degussa Aktiengesellschaft, Frankfurt am Main, Germany

[21] Appl. No.: 825,112

[22] Filed: Mar. 27, 1997

[30] Foreign Application Priority Data

Mar. 29, 1996 [DE] Germany ......................... 196 12 783.1

[51] Int. Cl.⁶ ................................................. C07C 27/00
[52] U.S. Cl. ........................... 568/898; 568/694; 502/81; 502/204; 502/213; 502/214
[58] Field of Search .................... 502/208, 213, 502/214, 81; 568/694, 898

[56] References Cited

U.S. PATENT DOCUMENTS 4,026,820  5/1977  Farha .
5,202,489  4/1993  Doumaux ................. 564/479
5,202,492  4/1993  Doumaux ................. 564/480
5,276,201  1/1994  Haas ........................ 568/491

OTHER PUBLICATIONS

CA 112:90417 "Changes of cordination polyhedra during oxidation" Zh. Struk +Khim (1989) 30(4) 180–2 Batsanov.

CA 125:167333 "Manufacture of alcohols by catalytic hydration of olefins" 1996 JP 08151339.

CA 123:348959 Catalysts for No. removal +their manufacture JP 07232075, 95.

*Primary Examiner*—Gary Geist
*Assistant Examiner*—Jean F. Vollano
*Attorney, Agent, or Firm*—Beveridge, DeGrandi, Weilacher & Young, L.L.P.

[57] ABSTRACT

A phosphoric acid catalyst on a shaped, inorganic support and its use for the hydration of olefins. At least 90 wt. % of the catalyst support consists of titanium dioxide and/or zirconium dioxide and has outstanding ageing stability under the hydrothermal conditions existing during hydration processes.

13 Claims, 2 Drawing Sheets

5,824,825

PHOSPHORIC ACID CATALYST AND ITS USE

INTRODUCTION AND BACKGROUND

The present invention relates to a phosphoric acid catalyst, method of making and its use for catalytic reactions under hydrothermal conditions. Hydrothermal conditions exist in chemical reactions in aqueous systems when the temperature is above the boiling point of water and the reaction is performed at pressures above atmospheric pressure.

A typical reaction under hydrothermal conditions is the hydration of olefins to give the corresponding alcohols in the presence of phosphoric acid as the catalyst or active component on a shaped catalyst support containing silicon dioxide.

This type of process is described, for example, in EP 0 578 441 A2. In this process, water and ethylene are reacted at temperatures from 225° to 280° C. and at pressures from 20 to 240 bar to give ethanol. In this case a water/ethylene molar ratio in the range 0.15 to 0.5 is used. The amount of feed measured in grams of water/ethylene mixture per minute and per milliliter of catalyst, can be selected to be within the range 0.01 to 0.1 g/(min×ml). Diethyl ether is produced as a by-product during this reaction.

The preparation of isopropanol by hydration of propylene takes place under similar conditions to those quoted above, but at a slightly lower temperature, in the range from 180° to 225° C. n-propanol is produced as a by-product in this reaction.

EP 0 578 441 A2 uses pellets made from synthetic silicon dioxide with a high crush strength, high porosity and low concentrations of metallic impurities as a catalyst support for the active component phosphoric acid. The pores in the support are used to take up the active component. The pore volume is therefore preferably larger than 0.8 ml/g. The average pore radius before use in the hydration process is in the range between 1 and 50 nm.

To reach optimum performance during hydration, EP 0 578 441 A2 prescribes a concentration of silicon dioxide in the support of at least 99 wt.%, with impurities of less than 1 wt.%, preferably less than 0.3 wt.%.

Catalysts undergo ageing during use, this becoming apparent through a reduction in activity and/or selectivity with time. Deactivation is frequently due to a reduction in the specific surface area of the support caused by high temperatures.

The specific surface area of the support is closely linked to its pore structure. In addition, high surface area solids mostly have a completely amorphous or largely amorphous structure which has the tendency to change into a thermodynamically stable state via crystallite growth and a reduction in the specific surface area.

It has been shown that catalyst supports which contain silicon dioxide are subject to this type of ageing. Hydrothermal conditions accelerate the ageing process.

This also applies to the catalyst support based on pyrogenically prepared silicon dioxide described in EP 0 393 356. The specific surface area is reduced by the merging of smaller pores to give larger pores.

At first, the pore volume hardly changes at all. This ageing takes place even though the pyrogenic silicon dioxide from which the support is made has an outstanding resistance to high temperature. When heated to temperatures of up to 1000° C. for a period of 7 days, the morphology of pyrogenic silicon dioxide does not change, according to tests using a scanning electron microscope (Schriftenreihe Pigmente No. 11: Grundlagen von AEROSIL®; Degussa company booklet, 5th edition, June 1993, page 20).

The object of the present invention is to provide a phosphoric acid catalyst on a catalyst support which has improved ageing stability when used under hydrothermal conditions.

SUMMARY OF THE INVENTION

The above and other objects are achieved in accordance with the invention by a phosphoric acid catalyst which contains 1 to 50 wt.% of $H_3PO_4$, with reference to the total weight of catalyst, on a shaped, inorganic support. A feature of the invention resides in that at least 90 wt.% of the support, with reference to the total weight of the pure support, consists of titanium dioxide and/or zirconium dioxide.

A further feature of the invention is a process of preparing the novel catalysts of the invention by coating the support particles with phosphoric acid. The support particles are immersed in an aqueous solution of phosphoric acid and soaked therein until the pore volume of the support is filled with the solution of phosphoric acid.

BRIEF DESCRIPTION OF DRAWINGS

The present invention will be further understood with reference to the drawings wherein.

DETAILED DESCRIPTION OF INVENTION

Figure 1:
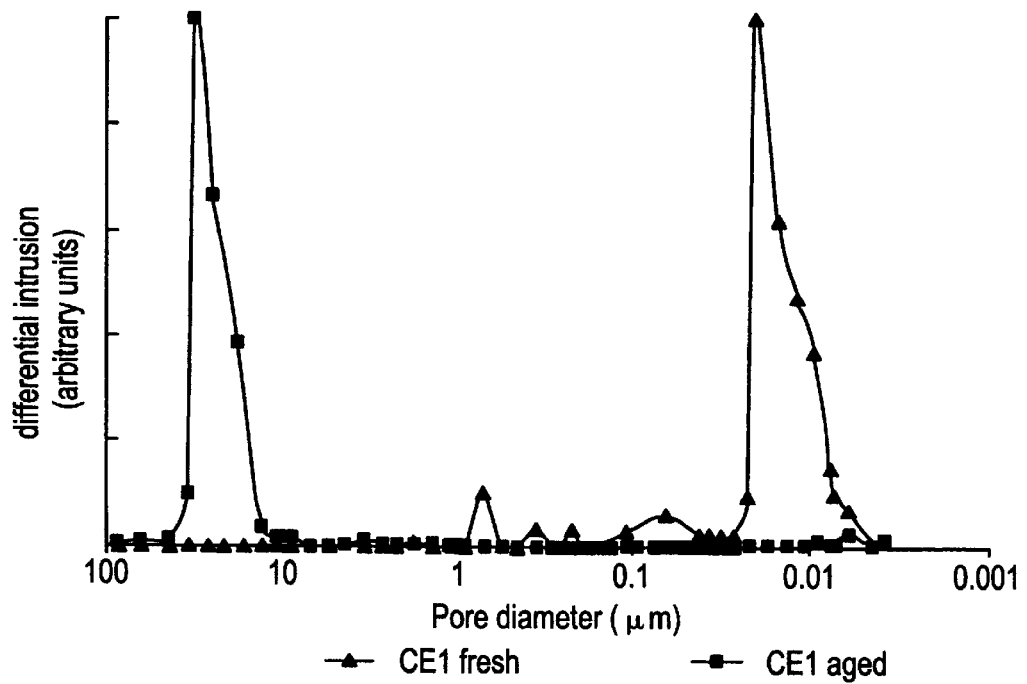
FIG. 1 is a graph of pore structure of a freshly prepared support made from pyrogenic silica and after coating the support with phosphoric acid and hydrothermal ageing.

Materials which are suitable as titanium dioxide and/or zirconium dioxide are those like the ones generally used for catalysis. They may be materials obtained by wet chemistry using the sulphate or chloride process or materials prepared by flame hydrolysis, so-called pyrogenic titanium or zirconium oxides. They consist of at least 90 wt.% titanium dioxide and/or zirconium dioxide. The balance consists of trace impurities contained in the titania and/or zirconia and optional forming aids and/or binder materials such as magnesium sterate, kaolin and bentonite. The loss on ignition of these support materials is generally less than 5 wt.%. They may contain, depending on the source of the starting materials, for example small proportions of silicon dioxide, aluminum oxide, iron oxide, alkali metal oxides and phosphorus pentoxide. Depending on the method of preparation, they may also contain a sulphate or chloride concentration of 1 to 2 wt.%. In the case of titanium dioxide, materials with anatase or rutile structures are suitable. The materials preferably used, due to their high porosity and high specific surface areas, are those which have, mainly (more than 80%) or exclusively, the anatase structure.

The materials mentioned above are processed in a known manner to give support particles. The support particles may be extrudates or granular substances or tablets. DE 40 12 479 A1, EP 0 394 677 B1 and EP 0 389 041 A1 describe suitable processes for preparing this type of particle from powdered materials.

To prepare catalysts according to the invention, the support particles are coated with phosphoric acid as an active component. For this purpose, the support particles are immersed in an aqueous solution of phosphoric acid and soaked with the same, wherein the pore volume in the support particles is filled with the solution of phosphoric acid. Phosphoric acid solutions with 15 to 85 wt.% of phosphoric acid, with reference to the total weight of solution, are used for this. Depending on the particular pore volume of the support particles, they can be coated with 1 to 50 wt.% of $H_3PO_4$, with reference to the total weight of final catalyst.

Catalysts prepared in this way are used for the hydration of olefins. A major field of application for the hydration of olefins is the hydration of ethylene to prepare ethanol and diethyl ether and also the hydration of propylene to prepare isopropanol. Reaction conditions disclosed in the prior art are used for these reactions.

The catalyst particles are introduced in the form of a bed in a high-pressure reactor and the reactants flow around them. In order to provide an adequate amount of the active component, phosphoric acid, per unit volume of the reactor, the pore volume of the moulded items should be 100 to 500 cm³ per liter of bulk volume. In the case of a bulk density of moulded items of, for example, 1000 g/l, therefore, the specific pore volume of the moulded items, with reference to their mass, should be in the range between 0.1 and 0.5 cm³/g.

The dimensions of the catalyst particles affects on the one hand the pressure loss in the reactor and on the other hand the accessibility of the phosphoric acid located in the pores to the reactants. If the dimensions are too small, the pressure loss is too high and if the dimensions are too large, the accessibility of the pores in the interior of the catalysts particles is reduced. Dimensions for the catalyst particles in the range of 1 to 10 mm have proven to be suitable. Catalyst particles with dimensions between 2 and 5 mm are preferably used.

To test the ageing stability of catalysts according to the invention and of comparison catalysts from the prior art, the pore structure of the freshly prepared supports, still not soaked with phosphoric acid, and of the aged catalysts, i.e. after soaking the support with phosphoric acid and hydrothermal ageing, was determined. Mercury porosimetry was used to determine the pore structure. Loading the catalyst particles with phosphoric acid has a negligible effect on the pore structure as determined using mercury porosimetry. Loading with phosphoric acid, however, does reduce the total pore volume which can be determined and must therefore be taken into account when calculating the actual pore volume.

Figure 2:
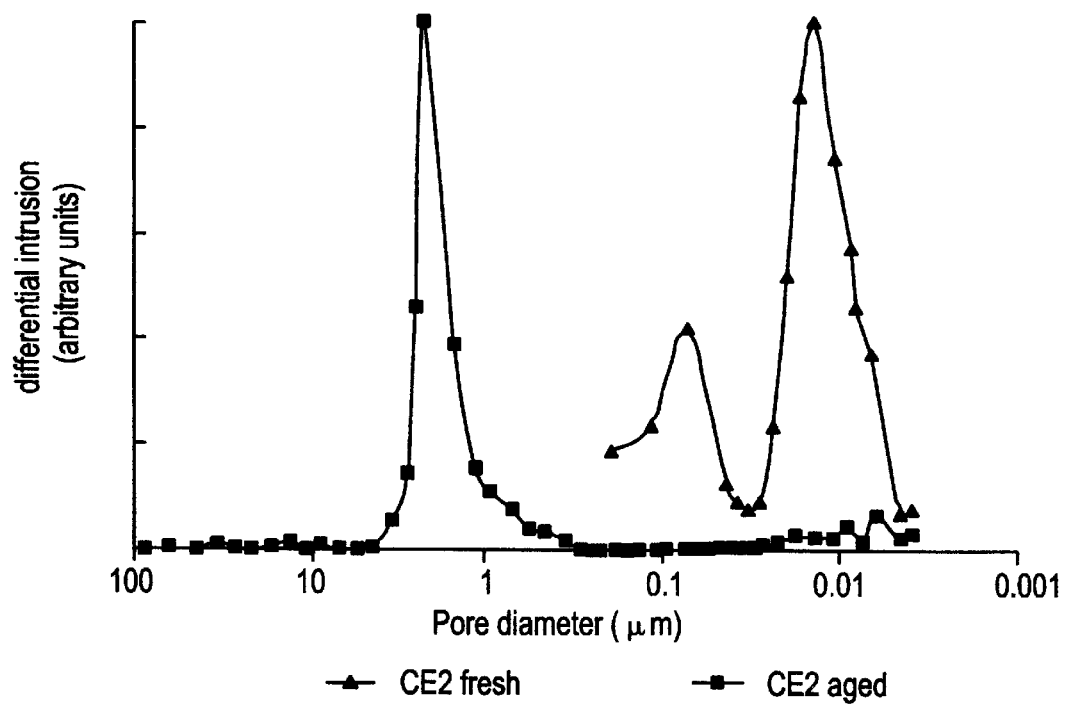
FIG. 2 is a graph of pore structure of a freshly prepared support made from natural silica and after coating the support with phosphoric acid and hydrothermal ageing.
Figure 3:
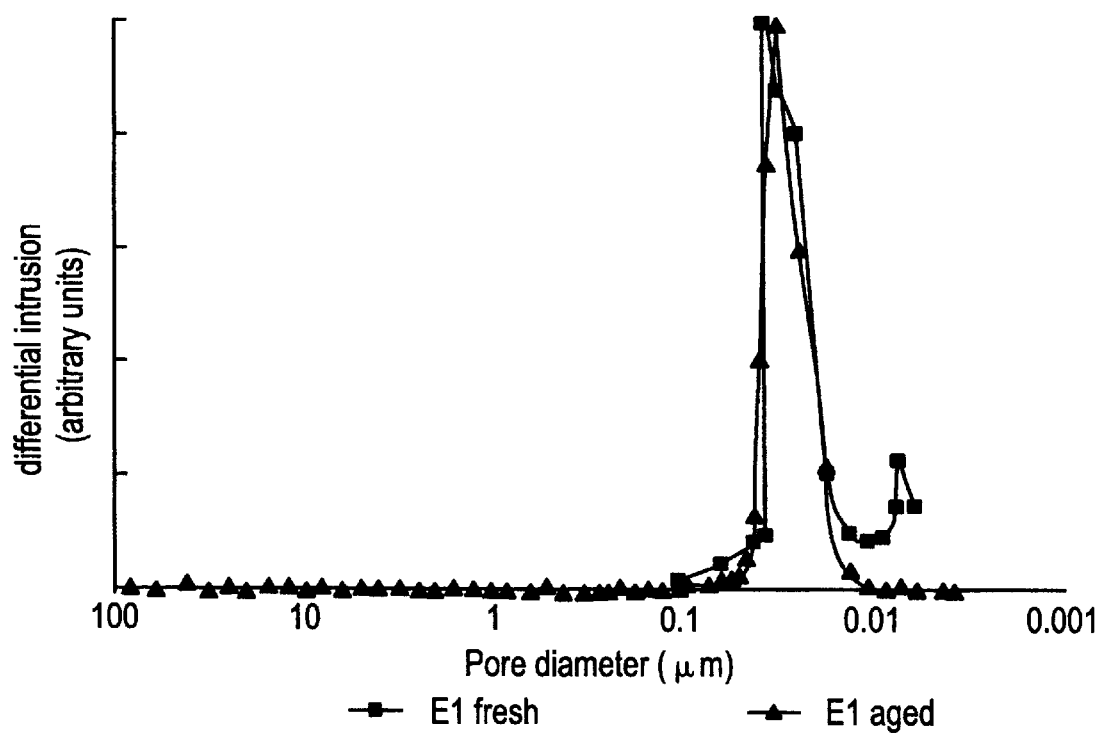
FIG. 3 is a graph of pore structure of a freshly prepared support made from titanium dioxide and after coating the support with phosphoric acid and hydrothermal ageing.

The pore distribution curves shown in FIGS. 1 to 3 give the differential penetration (intrusion) of mercury as a function of pore diameter. Arbitrary units were selected for differential intrusion and each curve extends over the available range in the diagram.

COMPARISON EXAMPLE 1

A catalyst support made from pyrogenic silica (AEROSIL®—support 350 from Degussa: specific surface area 180 m²/g; bulk density 490 g/l; total pore volume 0.8 cm³/g; tablets with a diameter of 6 mm and a thickness of 5.5 mm) was soaked with phosphoric acid (60 wt.%) and heated at 350° C. for 42 hours in a high-pressure unit under a steam pressure of 15 bar. The pore distribution of the freshly prepared support and of the aged catalyst was determined using Hg-porosimetry. The experimental pore distribution curves are shown graphically in FIG. 1 (CE1 fresh; CE1 aged).

The maximum of the pore distribution curve for the freshly prepared support was at pore diameters of 10 to 20 nm. Following hydrothermal ageing with phosphoric acid present in the pores, the maximum shifted to pore diameters from 20 to 30 µm. Thus the pores had grown by a factor of 1000. The total pore volume, however, had hardly changed as a result of the pore growth. Obviously, the small pores had merged to form larger pores.

COMPARISON EXAMPLE 2

A catalyst support based on natural silica (specific surface area 161 m²/g; pore volume 0.67 cm³/g; bulk density 550 g/l, spheres with a diameter of 5 mm) was soaked with phosphoric acid (60 wt.%) and heated in a high-pressure unit at 350° C. for 42 hours under a steam pressure of 15 bar. The pore distribution of the freshly prepared support and that of the aged catalyst was determined using Hg porosimetry. The experimental pore distribution curves are given graphically in FIG. 2 (CE2 fresh; CE2 aged).

Here again, hydrothermal treatment caused a dramatic growth in individual pore volume in this support material.

EXAMPLE 1

A catalyst support made from titanium dioxide (specific surface area 165 m²/g; pore volume 0.32 cm³/g; bulk density 900 g/l, extruded material with a diameter of 3 mm, length 2–4 mm; crystal structure largely anatase; concentration of $TiO_2$ greater than 97 wt.%) was soaked with phosphoric acid (60 wt.%) and heated in a high-pressure unit at 350° C. for 42 hours under a steam pressure of 15 bar. The pore distribution of the freshly prepared support and that of the aged catalyst was determined using Hg porosimetry. The experimental pore distribution curves are given graphically in FIG. 3 (E1 fresh; E1 aged) and it will be seen that the pore distribution curve essentially coincide.

The pore structure of this catalyst hardly changed at all, as compared with the freshly prepared support material, as a result of hydrothermal ageing. These measurements prove the very good long-term stability of phosphoric acid catalysts based on catalyst supports containing titanium dioxide.

Further modifications and variations of the foregoing will be apparent to those skilled in the art and are intended to be encompassed by the claims appended hereto.

German priority application 196 12 783.1 is relied on and incorporated herein by reference.

We claim:

1. A phosphoric acid catalyst comprising a shaped inorganic support having a pore volume, which contains 1 to 50 wt.% of $H_3PO_4$, with reference to the total weight of catalyst, wherein at least 90% of the support, with reference to the weight of pure support, consists of a member selected from the group consisting of titanium dioxide, zirconium dioxide and mixtures thereof, wherein said pore volume is filled with a solution of phosphoric acid.

2. The phosphoric acid catalyst according to claim 1 wherein said support further contains a member selected from the group consisting of silicon dioxide, aluminum oxide, iron oxide, an alkali metal oxide, phosphorous pentoxide and mixtures thereof.

3. The phosphoric acid catalyst according to claim 2 which further contains 1 to 2 wt. % of a sulfate or chloride.

4. The phosphoric acid catalyst according to claim 1 wherein said titanium dioxide is present in the anatase or rutile form.

5. The phosphoric acid catalyst according to claim 1 which has a specific pore volume of 0.1 to 0.5 cm$^3$/g.

6. The phosphoric acid catalyst according to claim 1 wherein the catalyst is in the form of particles of size of 1 to 10 mm.

7. A phosphoric acid catalyst comprising a shaped inorganic support having a pore volume, which contains 1 to 50 wt.% of H$_3$PO$_4$, with reference to the total weight of catalyst, wherein at least 90% of the support, with reference to the weight of pure support, consists of a member selected from the group consisting of titanium dioxide, zirconium dioxide and mixtures thereof, wherein said pore volume is filled with a solution of phosphoric acid, which catalyst when heated at 350° C. for 42 hours under steam pressure at 15 bar displays a pore distribution curve compared to a freshly prepared identical support that essentially coincides with the pore distribution curve for the freshly prepared support.

8. The phosphoric acid catalyst according to claim 1 which has a pore distribution curve after ageing that essentially coincides with a pore distribution curve for a freshly prepared support.

9. A process for the hydration of olefins comprising passing an olefin over the catalyst of claim 1 to produce an alkanol.

10. The process according to claim 9 wherein ethylene is hydrated to prepare ethanol and diethyl ether.

11. The process according to claim 9 comprising hydrating propylene to prepare isopropanol.

12. A process for preparing a phosphoric acid catalyst comprising providing shaped inorganic support particles formed of at least 90% by weight of a member selected from the group consisting of titanium dioxide, zirconium dioxide and mixtures thereof, immersing and soaking said particles in an aqueous solution of phosphoric acid until the pore volume of said particles is partially filled with said phosphoric acid.

13. A phosphoric acid catalyst comprising a shaped inorganic support having a pore volume, which contains 1 to 50 wt.% of H$_3$PO$_4$, with reference to the total weight of catalyst, wherein at least 90% of the support, with reference to the weight of pure support, consists of a member selected from the group consisting of titanium dioxide, zirconium dioxide and mixtures thereof, wherein said pore volume is filed with a solution of phosphoric acid, said catalyst being prepared by providing shaped or inorganic support particles formed of at least 90% by weight of titanium dioxide, zirconium dioxide or mixtures thereof, immersing and soaking said particles in an aqueous solution of phosphoric acid.

\* \* \* \* \*